United States Patent [19]

Haeger

[11] Patent Number: 4,534,977
[45] Date of Patent: * Aug. 13, 1985

[54] COMPOSITION OF MATTER COMPRISING A LOW BULK DENSITY LYOPHILIZED PREPARATION OF SODIUM PIPERACILLIN

[75] Inventor: Bruce E. Haeger, Highland Mills, N.Y.

[73] Assignee: American Cyanamid Company, Stamford, Conn.

[ * ] Notice: The portion of the term of this patent subsequent to Oct. 16, 2001 has been disclaimed.

[21] Appl. No.: 629,859

[22] Filed: Jul. 11, 1984

Related U.S. Application Data

[60] Division of Ser. No. 379,378, May 17, 1982, Pat. No. 4,477,452, which is a continuation-in-part of Ser. No. 247,586, Mar. 26, 1981, abandoned.

[51] Int. Cl.$^3$ .................... A61K 31/495; A23C 1/06
[52] U.S. Cl. .................... 514/196; 426/384; 426/385
[58] Field of Search ............... 424/250; 426/384, 385

[56] References Cited

U.S. PATENT DOCUMENTS

| | | | |
|---|---|---|---|
| 4,112,090 | 9/1978 | Saikawa et al. | 424/251 |
| 4,218,451 | 8/1980 | Feyen et al. | 424/250 |
| 4,226,769 | 10/1980 | Tsuji et al. | 424/256 |
| 4,477,452 | 10/1984 | Haeger | 424/250 |

OTHER PUBLICATIONS

Osol, Remington's Pharmaceutical Sciences, 15th ed., Mack Publishing Co., 1975, pp. 1361 and 1483.

*Primary Examiner*—Delbert R. Phillips
*Assistant Examiner*—F. T. Moezie
*Attorney, Agent, or Firm*—Gregg C. Benson

[57] ABSTRACT

This invention is concerned with a low bulk density lyophilized pharmaceutical parenteral dosage unit of Sodium Piperacillin and method of making same.

2 Claims, No Drawings

COMPOSITION OF MATTER COMPRISING A LOW BULK DENSITY LYOPHILIZED PREPARATION OF SODIUM PIPERACILLIN

This is a division of application, Ser. No. 379,378, filed May 17, 1982, U.S. Pat. No. 4,477,452, which is a continuation-in-part of application Ser. No. 247,586, filed Mar. 26, 1981, abandoned.

This invention comprises a low bulk density lyophilized pharmaceutical parenteral dosage unit of Sodium Piperacillin and a method of making said parenteral dosage unit.

Sodium Piperacillin, also known as 6-[2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid, sodium salt, is disclosed in U.S. Pat. No. 4,112,090 (Toyama Chemical Co.) wherein its utility as an antibacterial agent is established. The Toyama commercial product is prepared by filling a vial with 5 ml. of a 200 mg./ml. aqueous solution of sodium piperacillin per 1 g. dose and lyophilizing the contents; the dried cake having a volume of 4.94 cc/gm. When the physician is ready to administer the drug, he reconstitutes the vial with 3.3 ml. of water or other suitable parenteral diluent per gram of Sodium Piperacillin. The Sodium Piperacillin displaces 0.7 ml. of diluent per gram. The final volume is therefore 4.0 ml. per gram of reconstituted Sodium Piperacillin at a concentration of 250 mg./ml. The physician then withdraws the appropriate amount of solution from the vial with a syringe and administers the appropriate dose to the patient.

The difficulty with the above parenteral composition is that the physician must administer 4 mls. of solution per 1 gram dose. Piperacillin, like many penicillin derivatives, is hypertonic and therefore inherently causes pain upon intramuscular injection. Furthermore, the dosage limit for injection into the arm is approximately 2 milliliters, as the musculature simply will not tolerate larger interstitial volumes. The 4 milliliter dosage of the prior art per gram thus necessitates the less convenient procedure of giving injections in the buttocks. Even with injection in the buttocks, the large 4 milliliter per gram dosage means that distribution time is increased.

It is a purpose of this invention to provide a parenteral dosage unit form of Piperacillin and similar penicillin derivatives which decreases the injection volume from that known in the prior art by providing a more concentrated final product.

The difficulty with preparing a concentrated reconstituted preparation of lyophilized Sodium Piperacillin is that as concentration of the final product increases, reconstitution time also increases. One gram of Sodium Piperacillin represents a large volume of crystals, and the amount of diluent necessary to provide a concentrated reconstituted product is relatively small. The lyophilized cake solubilizes from the outside and the inherent resistance of the cake to wetting results in a gummy ball covered by a plastic film. At a final product concentration of 400 mg./ml., the reconstitution time may be as long as several minutes with continuous shaking. The time required to reconstitute such products has led to a discouragement of their use, with the result that more dilute preparations are used, with all their above-described disadvantages.

It is therefore another goal of this invention to provide a lyophilized parenteral dosage unit form of Piperacillin derivatives which provide a highly concentrated but easily reconstituted final product.

To this end a number of different approaches have been attempted. It was thought that the addition of a bulking agent might interrupt the homogeneity of the lyophilized Piperacillin cake to allow better water penetration. Five percent mannitol was selected for its innocuous nature and because it is rapidly soluble and easily lyophilized. This attempt was unsuccessful in overcoming the problem of reconstitution time. Likewise, the addition of a surface active agent such as Pluronic F68 or Polysorbate 80 at 0.2% levels was unsuccessful. The addition of cosolvents such as propylene glycol, polyethylene glycol 300, and ethanol at 10–60% levels in water was also attempted. Of these, only ethanol at concentrations of 20% or higher served to increase solvent penetration and decrease reconstitution time. However, the high level of ethanol required is expensive and the necessity of mixing a cosolvent system is too impractical for the administering physician, as the time spent offsets any gain in reconstitution time.

The present inventor has now discovered that increasing the porosity of the lyophilized cake itself by decreasing the concentration of the fill solution used before lyophilization results in a fluffy, low-bulk density lyophilized parenteral dosage unit with the desired characteristic of rapid reconstitution time.

The Sodium Piperacillin is dissolved in water at a concentration of from about 100 to 135 mg./ml. and the appropriate amount of solution to provide the desired dosage of Sodium Piperacillin is then filled into each vial. The vials are chosen for their ability to withstand the lyophilization procedure and for their ability to accept a suitable stopper which will allow for syringe withdrawal of the contents.

The Sodium Piperacillin is then frozen and lyophilized in the vial according to standard procedures well known to those skilled in the art. During the lyophilization step, the freeze-dried cake maintains the volume of the liquid fill dose and forms a crystalline loosely textured mass sealed under negative pressure. Since the volume of the liquid fill is 7.4–10 ml. per gram (depending on the selected fill concentration), the lyophilized cake is much larger and more porous than the five ml. per gram cake of the prior art. Following lyophilization the vials are sealed with appropriate septa for syringe compatability.

The above process may be modified to use fill concentrations of higher or lower than 100–135 mg./ml., although less successfully. At higher liquid fill concentrations the density of the lyophilized cake increases and the reconstitution time necessary to solubilize the Sodium Piperacillin at a concentration of 400 mg./ml. also increases, but at a greatly disproportionate rate. For example, increasing the liquid fill concentration by 15% increases the reconstitution time by over 100%. See Example 3. Alternatively, lower liquid fill concentrations may be used but the lower the liquid fill concentration, the greater the liquid fill volume required to provide a given amount of lyophilized derivative and the larger the lyophilization vial required. If a more dilute liquid fill concentration is used and a very large vial is necessary to contain the proportionately larger fill volume required, the final product after reconstitution to 400 mg./ml. will occupy only a relatively small fraction of the total vial volume. As a practical matter, the fill concentration should be within a range of 100–135 mg./ml., with a concentration of about 125 mg./ml. preferred.

In the preferred process, the Sodium Piperacillin is dissolved in water at a concentration of 125 mg./ml. Eight milliliters per gram dose of Sodium Piperacillin are then filled into a vial and the Sodium Piperacillin is lyopihlized to provide a cake with a volume of 8.31 cc/g. The vials are then stoppered with appropriate syringe septa.

When the physician is ready to administer a dose, he reconstitutes the lyophilized cake with 1.8 ml. of a suitable diluent per gram of Sodium Piperacillin. Examples of suitable diluents are, e.g., water or lidocaine hydrochloride, a local anesthetic which may be added to counteract the inherent pain of the injection due to the hypertonic nature of penicillin derivatives such as Piperacillin. The time necessary to reconstitute the lyophilized Sodium Piperacillin is approximately 1 minute with shaking. The final product provides 2.5 milliliters of a 400 mg./ml. solution per gram of Sodium Piperacillin, and an injection dose of 2.5 mls./gram as opposed to the 4 ml./gram dose of the prior art.

A further understanding of the invention can be had from the following non-limiting examples.

EXAMPLE 1

Determination of the Optimum Concentration of the Final Product—2 gms/vial

6-[2-(4-ethyl-2,3-dioxo-1-piperazinecarboxamido]-2-phenylacetamido]-3,3-dimethyl-7-oxo-4-thia-1-azabicyclo[3.2.0]heptane-2-carboxylic acid, sodium salt, was dissolved in water to a final concentration of 200 mg./ml. 10 mls. of this solution were filled into each of five vials and lyophilized by standard methods. Each of these lyophilized cakes was then reconstituted with a different amount of water to provide a series of final concentrations of Sodium Piperacillin with allowances made for the fact that each gram of Sodium Piperacillin displaces 0.7 ml. of water. These products were tested for pH, density, and viscosity by standard procedures. Solubilization time was measured by shaking the vials containing the lyophilized cake and the reconstitution water by hand and measuring the time necessary for the Sodium Piperacillin to go into solution. Syringeability was also estimated by measuring the time necessary to withdraw 1 ml. from a vial of final product. The results are given as follows:

| Sample | mls. water to reconstitute | Final* Volume | Final conc. (mg./ml.) | Avg. time to Solubilize (mins.) | pH | Density | Viscosity (cps) | Syringeability** 26 gauge | 21 gauge |
|---|---|---|---|---|---|---|---|---|---|
| 1 | 8.6 | 10 | 200 | 0.5 | 5.87 | 1.072 | 2.6 | Good | Good |
| 2 | 6.6 | 8 | 250 | 0.5 | 5.95 | 1.090 | 3.8 | Good | Good |
| 3 | 3.6 | 5 | 400 | 2.0 | 6.09 | 1.141 | 16.2 | Fair | Good |
| 4 | 2.6 | 4 | 500 | 5.75 | 6.16 | 1.173 | 65 | Poor | Fair |
| 5 | 1.93 | 3.33 | 600 | 25–30 | 6.27 | 1.206 | 314 | Poor | Poor |

*Each gram of Sodium Piperacillin displaces 0.7 ml. water
**Syringeability Test:
Good = 5–15 secs to withdraw 1 ml.
Fair = 20–30 secs to withdraw 1 ml.
Poor = >1 min to withdraw 1 ml.

EXAMPLE 2

Determination of the Optimum Concentration of the Final Product—1 g/vial

Following the procedure of Example 1, each of 5 vials were filled with 5 mls. of a 200 mg/ml solution of Sodium Piperacillin and lyophilized to provide 1 gram/vial. The vials were then diluted as above and the same tests were run. The results are given as follows:

| Sample No. | mls. water to reconstitute | Final* volume (mls) | Final conc. (mg./ml.) | Avg. time to Solubilize (min) | pH | Density | Viscosity (cps) | Syringeability** 26 gauge | 21 gauge |
|---|---|---|---|---|---|---|---|---|---|
| 1 | 4.3 | 5 | 200 | 0.75 | 5.83 | 1.073 | 2.6 | Good | Good |
| 2 | 3.3 | 4 | 250 | 0.75 | 5.92 | 1.090 | 3.8 | Good | Good |
| 3 | 1.8 | 2.5 | 400 | 2.75 | 6.07 | 1.141 | 16.2 | Fair | Good |
| 4 | 1.3 | 2.0 | 500 | 8.5 | 6.16 | 1.175 | 65 | Poor | Fair |
| 5 | 0.97 | 1.67 | 600 | 25–30 | 6.26 | 1.208 | 317 | Poor | Poor |

*Each ml. of Sodium Pipericillin displaces 0.7 ml. water.
**Syringeability Test:
Good = 5–15 secs to withdraw 1 ml.
Fair = 20–30 secs to withdraw 1 ml.
Poor = >1 min to withdraw 1 ml.

Based on the drastic increase in solubilization time and density and the drastic decrease in syringeability between the 400 and 500 mg/ml levels in Examples 1 and 2, it was concluded that 400 mg/ml is the uppermost practical reconstituted concentration to be used.

EXAMPLE 3

Relationship of Fill Concentration to Reconstitution Time

Sodium Piperacillin was prepared in four separate concentrations of 200, 166.7, 142.9, and 125 mg./ml. by dilution with water. An appropriate amount of each liquid fill concentration to provide 1 gram of Sodium Pipericillin was filled into a series of 4 vials and lyophilized. After lyophilization, each 1 gram cake was reconstituted with 1.8 mls. of water to a final volume of 2.5 mls. at a concentration of 400 1 mg./ml. Reconstitution time was measured and the results are as follows:

and shaken vigorously by hand until the lyophilized Sodium Piperacillin was solubilized, and the reconstitution time were measured and noted. The results are given in the following table:

| Sample | Dose Size (grams) | Quantity | Fill Conc. (mg/ml) | Fill Vol. (mls) | Diluent[a] (mls) | Final Vol.[b] (mls) | Final Conc. (mg/ml) | Avg. Reconstitution Time |
|---|---|---|---|---|---|---|---|---|
| 1 | 1 | 4 ea | 200 | 5 | 1.8 | 2.5 | 400 | 3 min. 16 sec. |
| 2 | 2 | 4 ea | 200 | 10 | 3.6 | 5.0 | 400 | 4 min. 24 sec. |
| 3 | 1.080 | 3 ea | 125 | 8.64 | 2.0 | 2.7[c] | 400 | 1 min. 15 sec. |
| 4 | 2.160 | 3 ea | 125 | 17.28 | 4.0 | 5.4[d] | 400 | 1 min. 9 sec. |

[a] Sterile water for injection USP
[b] 1 g Sodium Piperacillin displaced 0.7 ml diluent
[c] 2.5 mls. for injection
[d] 5.0 mls for injection

| Sample | Fill conc. (mg./ml.) | Ml Fill/vial | Reconstitution Mls. Water* | Final Conc. (mg/ml) | Average Reconstitution Time |
|---|---|---|---|---|---|
| 1 | 200 | 5 | 1.8 | 400 | 1 min 42 sec. |
| 2 | 166.7 | 6 | 1.8 | 400 | 1 min 16 sec. |
| 3 | 142.9 | 7 | 1.8 | 400 | 36 sec. |
| 4 | 125 | 8 | 1.8 | 400 | 15 sec. |

*Each gram of Sodium Piperracillin displaces 0.7 ml. of water.

EXAMPLE 4

Comparison with the Prior Art

The product of the present invention was compared with representative samples of the commercially available prior art.

A solution of Sodium Piperacillin in water was prepared at a concentration of 125 mg/ml and filled into vials with a fill volume of 8.64 mls. for a 1 gram dose (Sample 3) and 17.28 mls. for a two gram dose (sample 4). These vials contained an allowance for USP overfill; the 1 gram dose actually contained 1,080 mg. and the 2 gm. size actually contained 2,160 mg. This overfill allowance provided for full label claim potency by allowing for vial retention and syringe clearing losses. These samples were then lyophilized and stoppered.

Samples 3 and 4 above were then compared with commercially available Toyama Sodium Piperacillin (T-1220) which was prepared and filled at a concentration of 200 mg/ml with a fill volume of 5 mls. for the 1 g. dose (sample 1) and 10 mls. for the 2 g. dose (sample 2). The Toyama products contained no allowance for USP overfill.

Each sample was then diluted to 400 mg/ml with sterile water for injection USP, the vials were inverted

EXAMPLE 5

The following Table represents the amount of liquid fill of a 125 mg/ml solution necessary to provide a lyophilized product which when reconstituted will provide a 400 mg/ml final concentration, with allowance for USP overage:

| Label claim per Vial (g) | Mls. of 125 mg/ml solution | Actual mg/vial | Mls. to reconstitute to 400 mg/ml* | Final Conc.** (mg/ml) |
|---|---|---|---|---|
| 1 | 8.64 | 1,080 | 2.0 | 400 |
| 2 | 17.28 | 2,160 | 4.0 | 400 |
| 3 | 25.92 | 3,240 | 6.0 | 400 |
| 4 | 34.24 | 4,280 | 7.8 | 404 |
| 6 | 50.56 | 6,320 | 11.6 | 400 |

*Each gram of Sodium Piperacillin displaces 0.7 grams of water.
**Final concentration allows for USP overage to compensate for syringe clearance and product left in the vial.

I claim:

1. In a lyophilized pharmaceutical parenteral dosage unit of 6-[2-(4-ethyl-2,3-dioxo-1-piperazinecarboxamido)-2-phenylacetamido]-3,3-dimethyl-7-oxo-4-thia-1-azabicyclo[3.2.0]heptane-2-carboxylic acid sodium salt, the improvement which comprises a low bulk density cake of sodium piperacillin having a volume of from about 7 cc/gm to about 9 cc/gm, and having the capacity to be reconstituted to a concentration of about 400 mg/ml in less than 1 minute 30 seconds.

2. A lyophilized pharmaceutical parenteral dosage unit as recited in claim 1 wherein the cake has a volume of about 8.3 cc/gm.

* * * * *